United States Patent
Gao et al.

(10) Patent No.: US 10,352,908 B2
(45) Date of Patent: Jul. 16, 2019

(54) METHOD AND APPARATUS FOR THE DOWNHOLE IN-SITU DETERMINATION OF THE SPEED OF SOUND IN A FORMATION FLUID

(71) Applicant: Halliburton Energy Services, Inc., Houston, TX (US)

(72) Inventors: Li Gao, Katy, TX (US); Michael T. Pelletier, Houston, TX (US); Thurairajasingam Rajasingam, Kilcurry (IE); Arthur Cheng, Houston, TX (US); Paul Cooper, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 621 days.

(21) Appl. No.: 14/741,773

(22) Filed: Jun. 17, 2015

(65) Prior Publication Data
US 2015/0285058 A1    Oct. 8, 2015

Related U.S. Application Data

(63) Continuation of application No. 14/652,897, filed as application No. PCT/US2012/072190 on Dec. 28, 2012.

(51) Int. Cl.
*G01N 29/24* (2006.01)
*G01N 29/024* (2006.01)
(Continued)

(52) U.S. Cl.
CPC ....... *G01N 29/2412* (2013.01); *E21B 49/088* (2013.01); *G01N 29/024* (2013.01);
(Continued)

(58) Field of Classification Search
CPC ............ G01N 29/2412; G01N 29/024; G01N 29/025; G01N 29/222; G01N 29/2437; E21B 49/088
(Continued)

(56) References Cited

U.S. PATENT DOCUMENTS

| 5,430,259 A | 7/1995 | Warner |
| 5,619,423 A * | 4/1997 | Scrantz .............. G01N 29/2412 324/220 |

(Continued)

FOREIGN PATENT DOCUMENTS

| WO | WO 2003/097997 A1 | 11/2003 |
| WO | WO 2012/178013 A2 | 12/2012 |

OTHER PUBLICATIONS

International Search Authority, International Search Report and Written Opinion, dated Sep. 24, 2013, 12 Pages, Korean Intellectual Property Office.
(Continued)

*Primary Examiner* — Peter Macchiarolo
*Assistant Examiner* — Tarun Sinha
(74) *Attorney, Agent, or Firm* — Haynes and Boone, LLP

(57) ABSTRACT

An apparatus and a method for measuring a speed of sound in a fluid in a well bore may include a frame adapted to receive the fluid there through are provided. The apparatus includes an acoustic source mounted on the frame; an acoustic detector to measure a signal propagating through the fluid, the acoustic detector disposed proximate the frame at a known distance from the acoustic source; and a test circuit adapted to synchronize the acoustic detector with a signal propagating through the frame. A method to determine physical properties of a fluid in a geological formation including a shear wave anisotropy in the geological formation and the formation composition using the fluid density and the fluid speed of sound is also provided.

16 Claims, 12 Drawing Sheets

(51) Int. Cl.
*G01N 29/04* (2006.01)
*G01N 29/22* (2006.01)
*E21B 49/08* (2006.01)

(52) U.S. Cl.
CPC ......... *G01N 29/045* (2013.01); *G01N 29/222* (2013.01); *G01N 29/2437* (2013.01); *E21B 2049/085* (2013.01); *G01N 2291/011* (2013.01); *G01N 2291/02433* (2013.01); *G01N 2291/044* (2013.01); *G01N 2291/102* (2013.01)

(58) Field of Classification Search
USPC .......................................................... 73/579
See application file for complete search history.

(56) References Cited

U.S. PATENT DOCUMENTS

| | | |
|---|---|---|
| 6,354,146 B1 | 3/2002 | Birchak et al. |
| 6,874,361 B1 | 4/2005 | Meltz et al. |
| 7,150,317 B2 | 12/2006 | Barolak et al. |
| 8,321,133 B2 | 11/2012 | Hsu et al. |
| 2005/0011279 A1* | 1/2005 | Takeda .................... G01F 1/667 73/861.26 |
| 2007/0256828 A1 | 11/2007 | Birchak et al. |
| 2008/0149416 A1* | 6/2008 | Coates ..................... G01V 1/40 181/121 |
| 2008/0173100 A1* | 7/2008 | Davis ...................... G01F 1/667 73/861.27 |
| 2009/0105957 A1* | 4/2009 | Hsu ........................ E21B 49/081 702/12 |
| 2009/0105969 A1* | 4/2009 | Saylor .................... G01D 9/005 702/47 |
| 2011/0308332 A1* | 12/2011 | Blessum ................... G01L 1/24 73/862.624 |
| 2012/0182831 A1 | 7/2012 | Cooper et al. |

OTHER PUBLICATIONS

Supplementary Partial European Search Report issued for EP 12890893, dated Jul. 29, 2016, 5 pages.

* cited by examiner

FIG. 7A
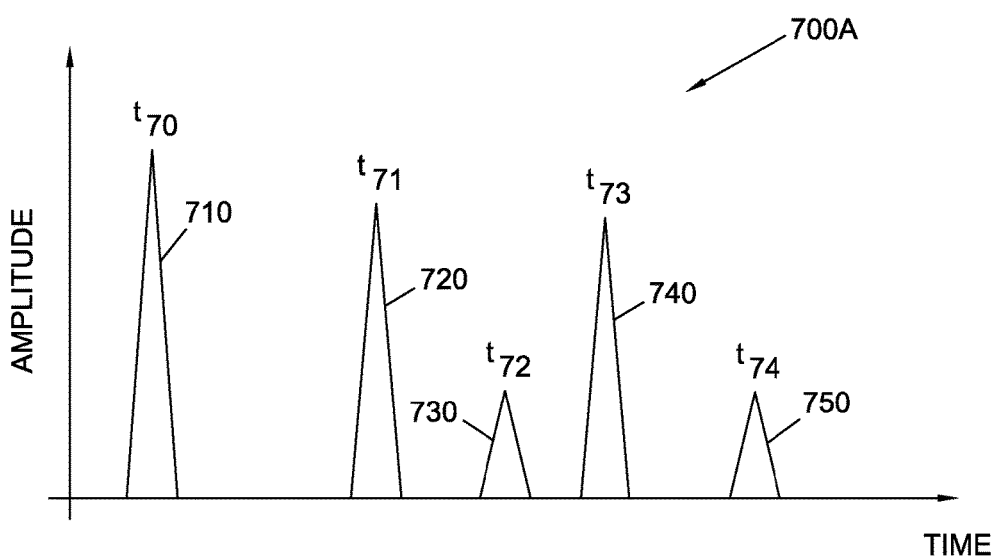
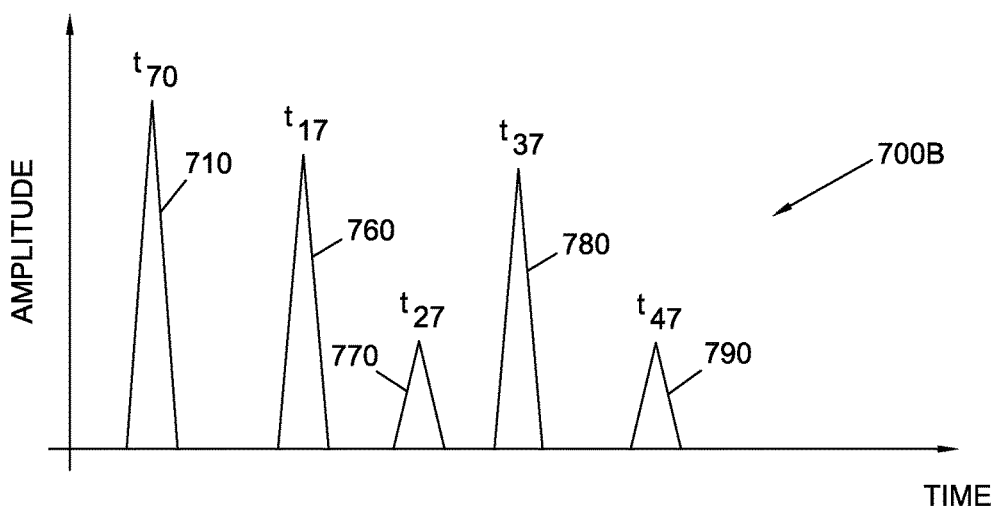
FIG. 7B

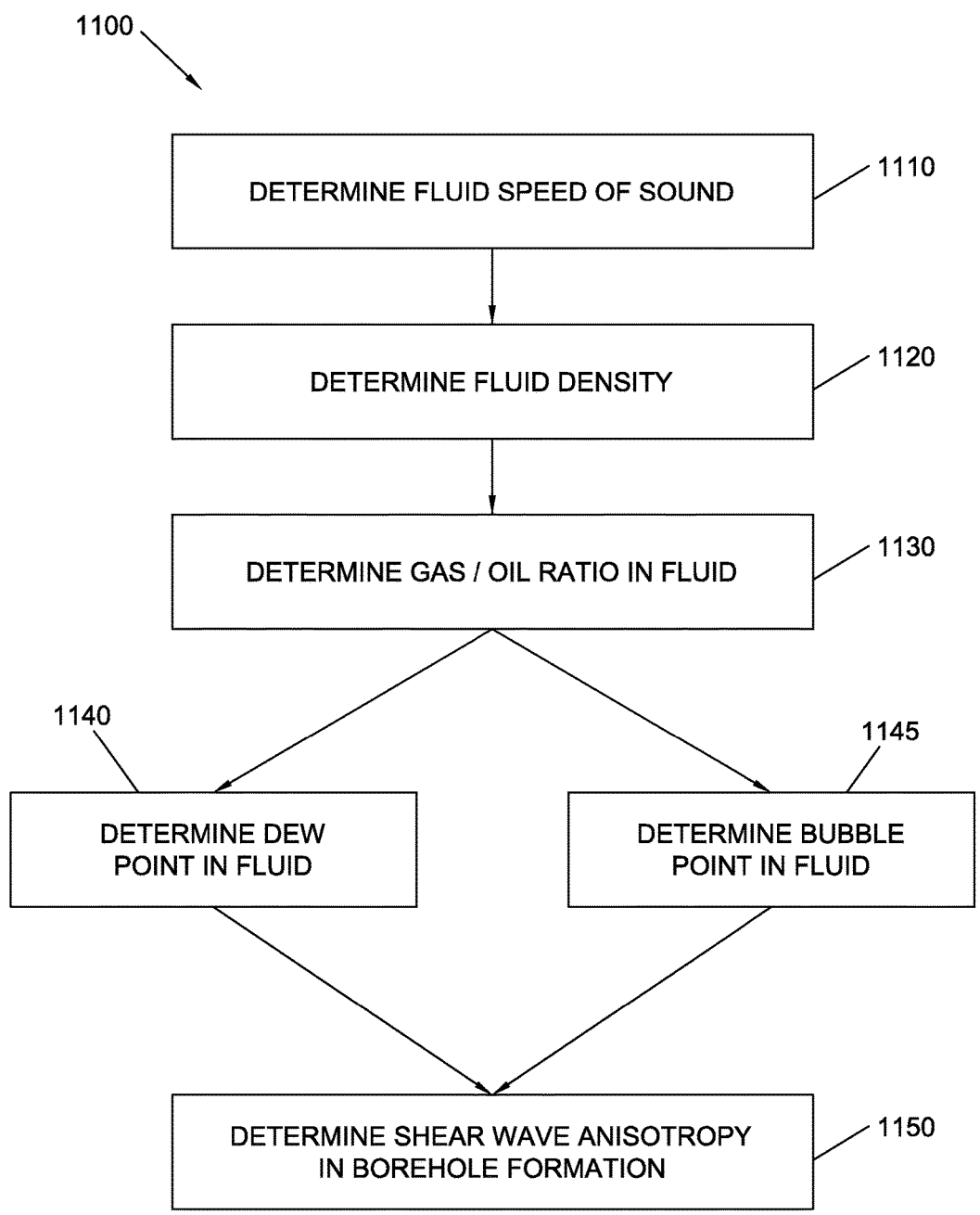

METHOD AND APPARATUS FOR THE DOWNHOLE IN-SITU DETERMINATION OF THE SPEED OF SOUND IN A FORMATION FLUID

PRIORITY

The present application is a Continuation Application of U.S. application Ser. No. 14/652,897, filed on Jun. 17, 2015, which is a National Stage patent application of International Patent Application No. PCT/US2012/072190, filed on Dec. 28, 2012, the benefits of which are claimed and the disclosures of which are incorporated herein by reference in their entirety.

BACKGROUND

1. Technical Field

Embodiments disclosed herein relate generally to the field of borehole formation testing and acoustic logging. More particularly, embodiments disclosed herein are related to measurement of the speed of sound in a formation fluid.

2. Description of Related Art

In the field of borehole acoustic logging for oil and gas exploration and extraction, in situ measurement of physical properties of earth formations is desired. Earth formations typically include different types of solid substrates in a variety of physical arrangements such as layers, rock beds, sand embankments, and others. The solid materials may be mixed with fluids and suspensions including mud, water, oil, and gas among other components. Due to the complexity of earth formation compositions, a wide variety of parameters is collected to obtain properties such as Gas-Oil Ratio (GOR), or shear wave anisotropy. GOR is a volumetric measure providing the ratio of gas to oil at atmospheric pressures, once the liquid is extracted from the "downhole" formation at high pressures. The shear wave anisotropy is related to the depositional history and the amount and maturity of hydrocarbons in a gas shale. One of the parameters used to extract formation properties is the formation fluid density. However, to obtain more accurate values of the physical properties of the earth formations, the speed of sound in the fluid component is a desired parameter. For example, a linear relation has been found between GOR and the fluid speed of sound.

Therefore, it is of practical importance to accurately measure formation fluid speed of sound in addition to other parameters used to determine physical properties of the soil formation.

BRIEF SUMMARY

According to some embodiments an apparatus for measuring a speed of sound in a fluid in a well bore may include a frame adapted to receive the fluid there through; an acoustic source mounted on the frame; an acoustic detector to measure a signal propagating through the fluid, the acoustic detector disposed proximate the frame at a known distance from the acoustic source; and a test circuit adapted to synchronize the acoustic detector with a signal propagating through the frame.

According to some embodiments a method to determine fluid speed of sound may include providing, at a first time, an acoustic impulse to a first location of a sensor frame having a hollow core filled with a fluid; synchronizing an acoustic detector to operate in a time interval associated to the first time; detecting, at a second time and at a second location, the acoustic impulse on the sensor frame; and determining a fluid speed of sound using the first location, the second location, the first time, and the second time.

In some embodiments, a method to determine physical properties of a fluid in a geological formation may include determining a speed of sound in the fluid and a density of the fluid using a sensor; determining a gas/oil ratio (GOR) in the fluid using a lookup table including a plurality of speed of sound values in the fluid forming a linear relation with a plurality of GOR values; determining a shear wave anisotropy in the geological formation using the fluid density and the fluid speed of sound; and determining a formation composition from the shear wave anisotropy.

These and other embodiments will be described in further detail below, with reference to the following drawings.

BRIEF DESCRIPTION OF THE DRAWINGS

FIG. 7A shows an acoustic signal as a function of time in a detector, according to some embodiments.

FIG. 7B shows an acoustic signal as a function of time in a detector, according to some embodiments.

FIG. 11 shows a flow chart for a method to determine physical properties of a fluid and a downhole formation, according to some embodiments.

Wherever possible, the same reference numbers are used throughout the drawings to refer to the same or like elements.

DETAILED DESCRIPTION

An apparatus and a method to determine formation fluid speed of sound on a wireline formation tester (WFT) or logging while drilling (LWD) formation tester (LWDFT) are disclosed. In both WFT and LWDFT acoustic logging tools, knowledge of the effect of drilling mud in the well bore is desirable to produce accurate and robust acoustic logging results and interpretation. In this process, the speed of sound in drilling mud is a relevant parameter. Sensor embodiments provided herein generate an acoustic impulse signal into a conduit carrying fluid in a downhole tool such as a WFT or an LWD tester. The fluid speed of sound inside the conduit is determined by monitoring the transit time of the acoustic impulse from the source to a detector at a known distance away from the source.

The apparatus can be configured on an existing vibrating tube density sensor. Formation fluid speed of sound determined using such an apparatus is useful in various aspects of formation evaluation. In some embodiments, a fluid speed of sound may be used to derive a gas/oil ratio (GOR or liquid yield) which is known to be highly correlated to speed of sound and density. In some embodiments, a fluid speed of sound may be used to determine a dew point pressure of gas/condensates. In some embodiments, the fluid speed of sound is used for calibration of seismic models for conventional surface seismic and borehole seismic works. Further according to some embodiments, a fluid speed of sound is used to determine fluid type and composition. In some embodiments, a fluid speed of sound is used to determine the speed of sound in drilling mud. In some embodiments, the speed of sound in a fluid is used to derive the shear wave modulus component $C_{66}$ in a Vertical Transverse Isotropic (VTI) formation having a vertical symmetry axis (such as a shale). In such embodiments, a $C_{66}$ component may be obtained from Stoneley wave speed measurement, combined with a measurement of the speed of sound in a fluid. A Stoneley wave is a surface wave propagating along the solid-fluid interface of the borehole. For example, a Stoneley wave may propagate along the Z-axis in the configuration shown in FIG. 1A.

Figure 1A:
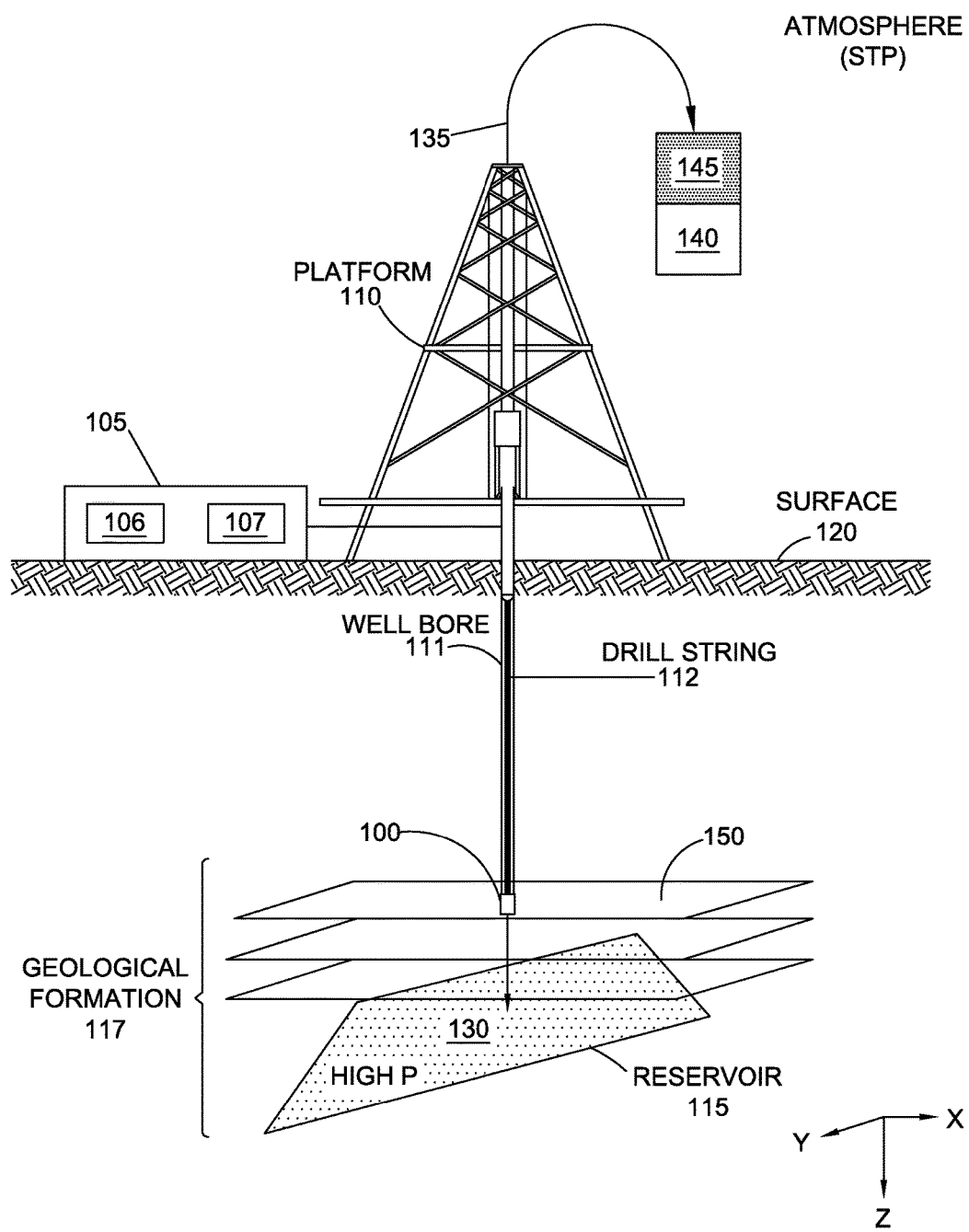
FIG. 1A shows a hydrocarbon extraction platform according to some embodiments.

FIG. 1A shows a hydrocarbon extraction platform 110 according to some embodiments. Platform 110 is in an atmospheric environment at approximately standard temperature and pressure (STP) conditions. STP conditions are 1 atmosphere (1 atm) of pressure and 15° C. of temperature (about 59° F.). Platform 110 may include drill string 112 extending underground in a well bore or borehole 111. At an underground point drill string 112 makes contact with reservoir 115, which may include live crude oil 130. One of ordinary skill would recognize that reservoir 115 may have different embodiments depending on the geological conditions of well bore 111. According to one of ordinary skill, any hydrocarbon other than or in combination with live crude oil may be found at the downhole in well bore 111. A mechanism that may include valves, pumps, and other components (not shown in FIG. 1A) directs crude oil 130 to the surface and out of platform 110 through outlet 135. According to embodiments disclosed herein, platform 110 may include a device to perform WFT and/or LWD. The device may include a controller 105 disposed near or on the surface 120, and a sensor 100 disposed downhole in the well bore 111. Controller 105 may include a processor circuit 106 and a memory circuit 107. Controller 105 is connected to sensor 100 in order to provide power, and control commands to sensor 100. In some embodiments, for example in a wireline configuration, controller 105 is electrically connected to sensor 100. In some embodiments, such as in LWD applications, power may be provided to sensor 100 locally, near the tip of drill string 112, by a battery or a downhole turbine generator powered by drilling fluid flow. Controller 105 also retrieves data from sensor 100 and performs data analysis and processing with processor circuit 106 and memory circuit 107.

Crude oil 130 is a liquid containing a mixture of hydrocarbons forming oil, and dissolved gases such as methane $CH_4$, carbon dioxide, $CO_2$, and others. The dissolved gases will form a gaseous phase at atmospheric conditions. Thus, when crude oil 130 is released into the atmosphere it contains two main phases, a liquid phase 140, which is the commonly known 'oil,' and a gas phase 145 containing natural gas, including methane and other gases.

FIG. 1A also shows sensor 100 for measuring formation fluid speed of sound in the well bore 111. The coordinate axis system XYZ in FIG. 1A illustrates the Z-axis in the longitudinal direction of well bore 111. The Z-axis does not have to be perpendicular to the surface as well bore 111 may change orientation relative to the surface as it is being formed. Formation planes 150 oriented in the XY direction illustrate different layers of material that may include rocks, sediments, sand, crude oil, natural gas, water, and other materials. According to some embodiments, the geological formation 117 encountered by drill string 112 may be approximately isotropic in planes 150 substantially parallel to the XY plane (VTI formation). In such embodiments, a formation fluid speed of sound may be used to measure stress properties of materials when the formation 115 includes layers approximately symmetric across formation planes 150 in FIG. 1A. It should be understood by those skilled in the art that geological formations may not be absolutely orthogonal to the Z axis. In some embodiments, the geological formations may divert at an angle relative to the Z-axis, along the direction of the well bore 111. Those skilled in the art will recognize that embodiments disclosed herein may be adapted to operate in configurations where the geological formation forms an oblique angle relative to well bore 111.

Figure 1B:
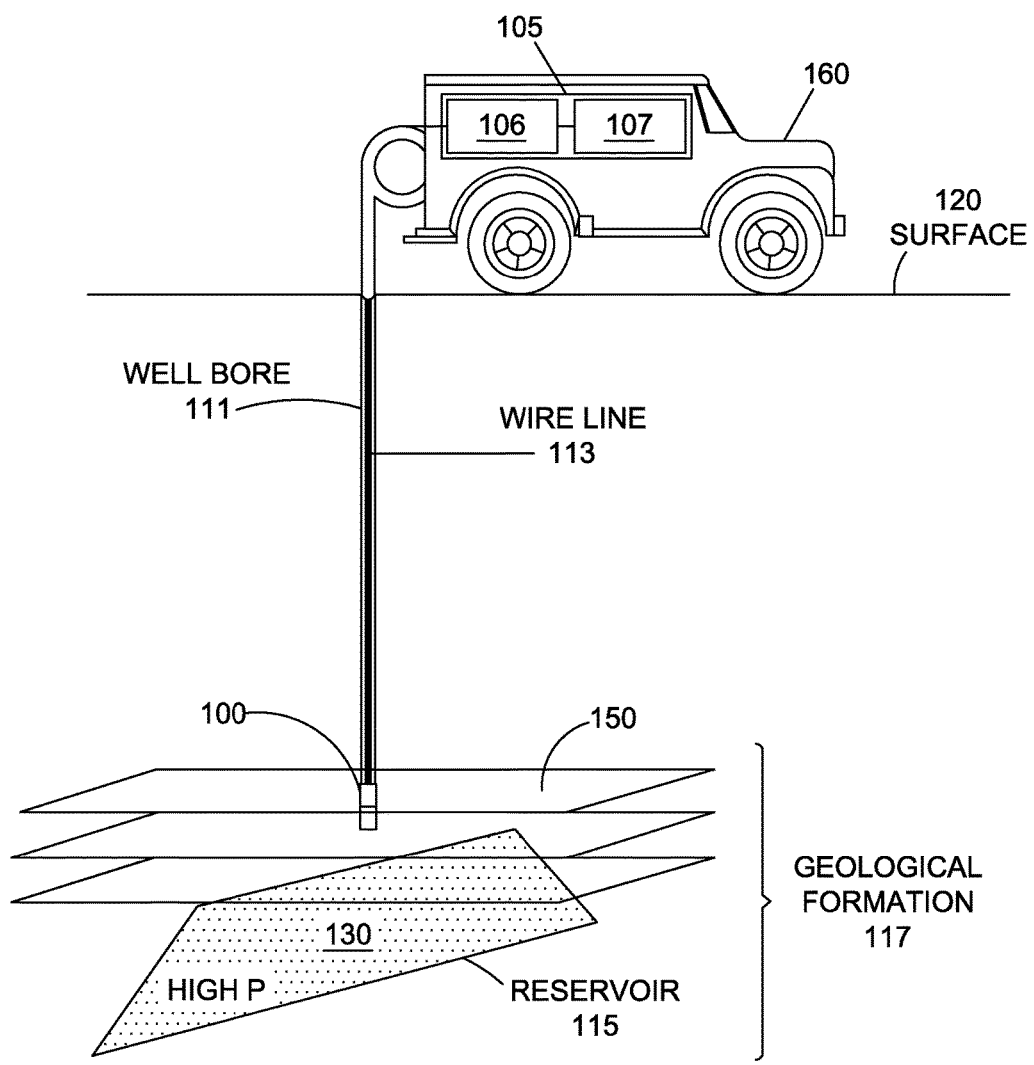
FIG. 1B shows a wireline formation tester (WFT) setup, according to some embodiments.

FIG. 1B shows a wireline formation tester (WFT) configuration, according to some embodiments. In a WFT configuration, a well bore may already be drilled below the surface, and a geological formation may be measured using a sensor as disclosed herein. The sensor may be displaced up and down the well bore using a wireline supported by a WFT test station, which may be a mobile unit. In the embodiments depicted in FIG. 1B, wireline 113 is used to support sensor 100. In some embodiments, wireline 113 may also provide power to sensor 100 and transmit data form sensor 100 to controller 105. Controller 105 including processor circuit 106 and memory circuit 107 may be included in mobile unit 160, above surface 120. The geological formation tested by a WFT configuration may have any orientation relative to surface 120. For example, in embodiments as shown in FIG. 1B geological formation 117 may include symmetry planes 150 oriented substantially parallel to the XY plane shown in the figure. Accordingly, in some embodiments of a WFT configuration, well bore 111 may be in the proximity of reservoir 115 having hydrocarbons 130 at a high pressure.

In some embodiments, an LWD configuration or a WFT configuration may be used in a subsea environment. In a subsea environment, surface 120 in FIGS. 1A and 1B may be the ocean floor. Accordingly, in a subsea environment drill string 112 or wireline 113 may have a portion submerged in water. Also, in a subsea environment platform 110 may be floating on water (cf. FIG. 1A), and mobile unit 160 may be a boat (cf. FIG. 1B).

Figure 2:
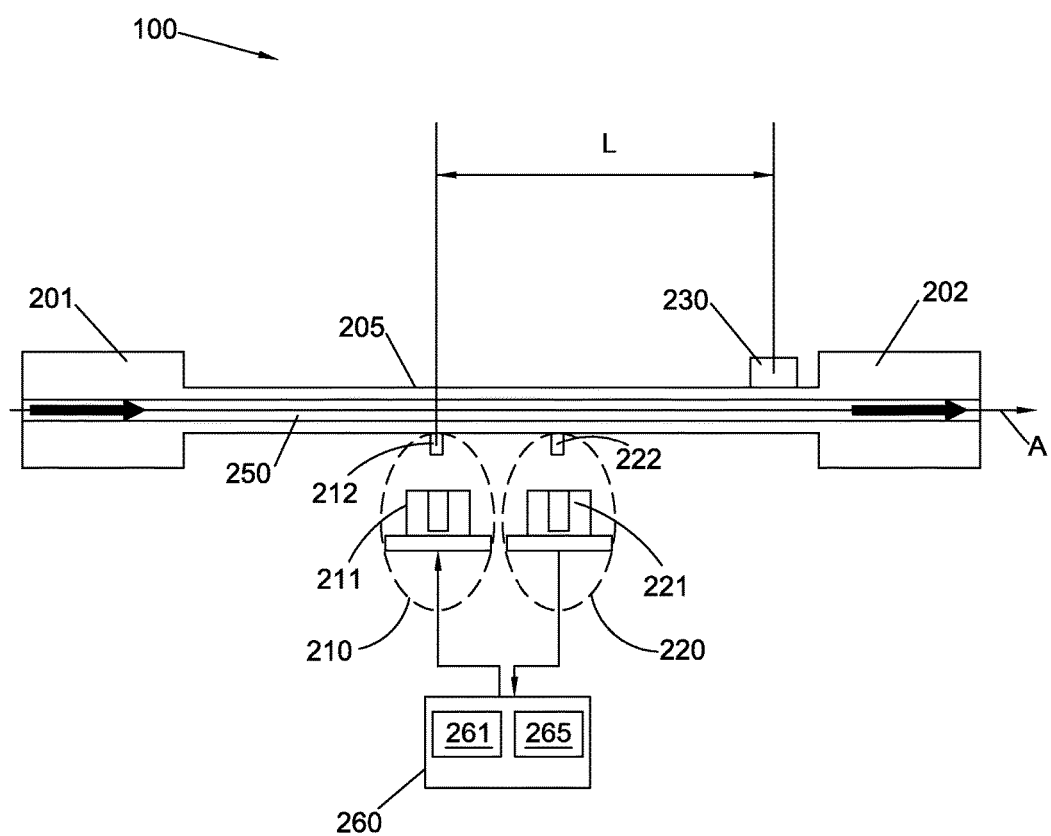
FIG. 2 shows a schematic view of a sensor for measuring the speed of sound in a fluid, according to some embodiments.

FIG. 2 shows a schematic view of a sensor 100 for measuring the speed of sound in a fluid, according to some embodiments. Sensor 100 includes a frame 205 having end portions 201 and 202. End portions 201 and 202 have more mass and a different geometry (e.g. generally a larger diameter), than a middle portion of frame 205. In some embodiments, frame 205 may be a tube in the shape of a hollow cylinder, and may be made of a hard material such as platinum, or titanium, or any other metal. In some embodiments, frame 205 may be made of a material such as a glass or a ceramic material. Inside frame 205, a fluid 250 passes at a flow rate from the exterior of sensor 100. Fluid 250 may include crude oil, water, mud, and silt from a downhole environment (e.g., from well bore 111). According to some embodiments, sensor 100 includes a longitudinal axis 'A' oriented in the direction of well bore 111 created by drill string 112. For example, axis A may be oriented along the Z-direction in a vertical well bore configuration (cf. FIG. 1). One of ordinary skill would recognize that the orientation of longitudinal axis A relative to coordinate system XYZ is not limiting for the functionality of sensor 100. For example, in some embodiments sensor 100 may be oriented along the X-axis, or along the Y-axis, or along an arbitrary direction relative to the XYZ coordinate system.

In some embodiments, sensor 100 may include an acoustic source 210, an acoustic detector 220, and an accelerometer 230. For example, acoustic source 210 and acoustic detector 220 may be part of an existing vibrating tube density sensor. Accordingly, in some embodiments acoustic source 210 may be mounted on a tube, and acoustic detector 220 may be disposed proximate to the metallic tube, at a known distance from the detector. In some embodiments, acoustic detector 220 may be disposed on the tube, making physical contact with the vibrating tube. In some embodiments, acoustic detector 220 may be disposed at a distance from the tube, and mechanically coupled to the tube.

Acoustic source 210 may include a coil 211 and a magnet 212. Likewise, acoustic detector 220 may include a coil 221 and a magnet 222. Thus, a current through coil 211 in acoustic source 210 generates a magneto-motive force that pushes magnet 212 against frame 205, generating an acoustic wave. The acoustic wave propagates through frame 205 and moves magnet 222 in detector 220, which in turn generates a current in coil 221. Acoustic detection includes measurement of the current in detector 220. In some embodiments, sensor 100 may include a test circuit 260 having a current source 261 providing the current to coil 211, and a measurement circuit 265 to measure the current from coil 221. By applying an AC current at varying frequencies to coil 211, a broad band of acoustic frequencies may be propagated through frame 205. Also, by applying an AC current at varying frequencies to coil 211, a broad band of acoustic frequencies may propagate through fluid 250 inside frame 205. By measuring the amplitude of the sensor response in detector 220 using measurement circuit 265, a resonance frequency may be obtained for the acoustic frequencies propagating through fluid 250. The resonance frequency is a well-known function of the density of fluid 250 inside frame 205. Thus, the formation fluid density may be obtained by measuring the resonance acoustic frequency of sensor 100 using acoustic source 210 and acoustic detector 220. In addition to the formation fluid density, sensor 100 may be used to measure speed of sound in fluid 250, as follows.

Accelerometer 230 is located at a distance L from source 210. A current pulse from current source 261 through coil 211 generates a magneto-motive force, i.e. an "impact force," that pushes magnet 212 against frame 205. The impact force produced by magnet 212 on frame 205 may last for a pre-selected amount of time. In some embodiments, the impact force lasts for an amount of time substantially shorter than L/c where c is the speed of sound in the frame material. Accordingly, the impact force may last for about one millisecond (1 ms). The impact force on frame 205 produces at least two acoustic impulses that travel through frame 205. At least one acoustic impulse travels through the hard shell of frame 205, and at least a second acoustic impulse travels through fluid 250. The acoustic impulses generated by source 210 produce impulsive signals in accelerometer 230. In some embodiments, accelerometer 230 measures vibrations of frame 205 generated by the acoustic impulses traveling through the frame. The speed of sound may be determined by knowing the distance L separating source 210 and accelerometer 230 and by measuring the time it takes for the acoustic impulse to travel from source 210 to accelerometer 230. Accordingly, in some embodiments test circuit 260 is adapted to synchronize acoustic detector 220 and accelerometer 230 using an acoustic impulse travelling through the hard shell of frame 205. For example, test circuit may be configured to operate detector 220 and accelerometer 230 in a time interval associated to the time at which source 210 generates the acoustic impulse. Thus, sensor 100 may use a signal propagating through frame 205 to establish the start time of the second acoustic impulse traveling through fluid 250. Test circuit 260 may collect a signal from accelerometer 230 at a detection time within the time interval.

Embodiments of accelerometer 230 may use a magneto-motive principle similar to the principle of operation of acoustic source 210. In some embodiments, accelerometer 230 may include an optical mechanism to measure vibrations of frame 205 at a point on the surface of frame 205 located a distance L from acoustic source 210. For example, an optical mechanism in accelerometer 230 may include a laser beam being reflected off of the point in the surface of frame 205 and detected by a detector (not shown) divided into separate quadrants. A vibration in frame 205 may produce a deflection of the laser beam reflected to a different quadrant in the detector. In some embodiments, an optical mechanism in the accelerometer 230 may include a gas bubble in a fluid container, the container being in physical contact with frame 205. In that embodiment, a vibration in frame 205 produces a motion of the bubble in the fluid container which may be detected by a laser beam or an imaging camera. In some embodiments, accelerometer 230 may include a fluid enclosed in a container having a pressure sensor attached to it, where the container is in physical contact with frame 205. A vibration in frame 205 produces a pressure wave in the fluid within the container, which may be detected by the pressure detector. In some embodiments, accelerometer 230 may be a piezoelectric material or other electro-mechanic transducer driven by an electrical circuit and providing a signal to the electrical circuit.

According to some embodiments, measurement of the fluid density and measurement of the fluid speed of sound may be independent measurements. In some embodiments, processor circuit 106 may include an application specific integrated circuit (ASIC) to perform a fluid density measurement and a fluid speed of sound measurement from data provided by sensor 100. For example, a fluid density measurement may include scanning the frequency of the acoustic excitation through a narrow frequency band for an extended period of time. In some embodiments, a fluid speed of sound measurement includes generating an acoustic impulse having a short time window, including a wide range of frequencies. In some embodiments, the range of frequencies is centered on a resonance frequency of frame 205 having fluid 250 inside. Thus, according to some embodiments sensor 100 provides a density measurement and a speed of sound measurement for a formation fluid. The two measurements may be used to determine physical properties of the formation 115 and the formation fluid.

Figure 3:
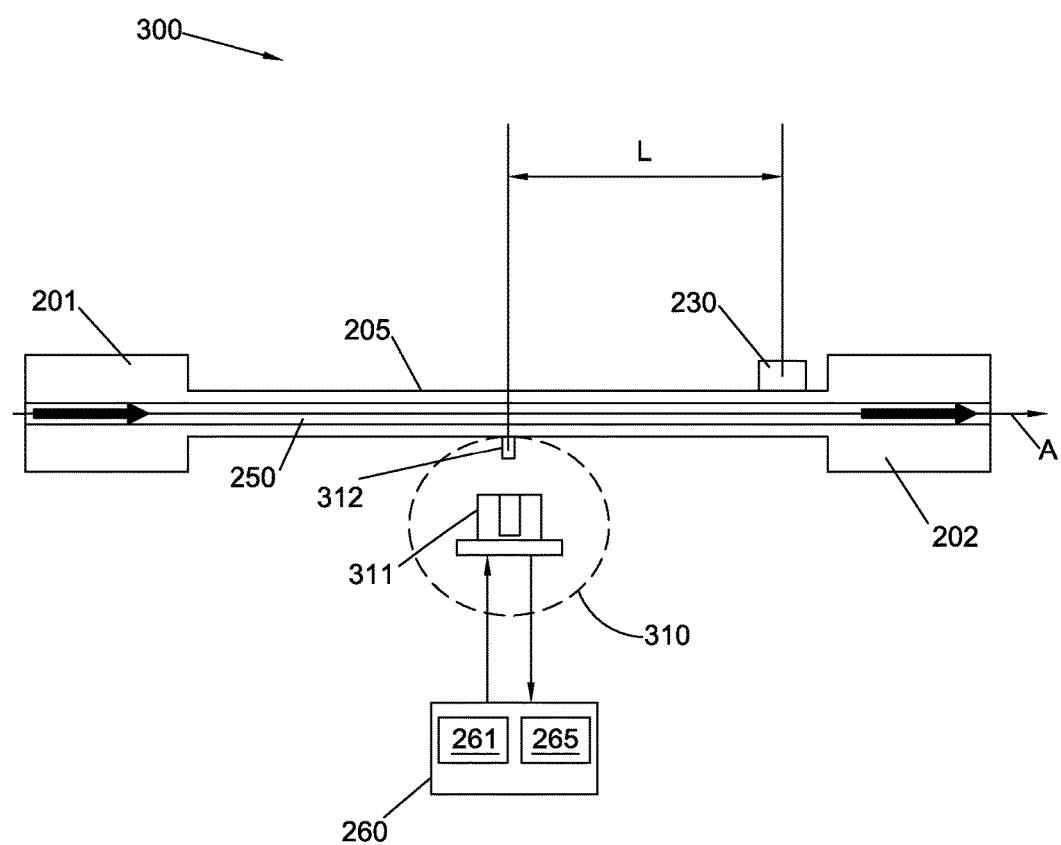
FIG. 3 shows a schematic view of a sensor for measuring the speed of sound in a fluid, according to some embodiments.

FIG. 3 shows a schematic view of a sensor 300 for measuring the speed of sound in a fluid, according to some embodiments. Sensor 300 includes frame 205, frame endings 201 and 202, and fluid 250 having a flow rate as described in detail above in relation to sensor 100 (cf. FIG. 2). An acoustic source 310 may include coil 311 and magnet 312, operated by test circuit 260 having current source 261 and measurement circuit 265, as described in detail above in relation to acoustic source 210 in sensor 100 (cf. FIG. 2). Accelerometer 230 may be placed at a distance L from acoustic source 310, as in sensor 100. The operation of sensor 300 to measure a speed of sound in fluid 250 is as described in relation to sensor 100, in FIG. 2 above. Accordingly, sensor 300 is an embodiment of a sensor wherein a single coil 311 and a single magnet 312 are used to generate acoustic signals.

Figure 4:
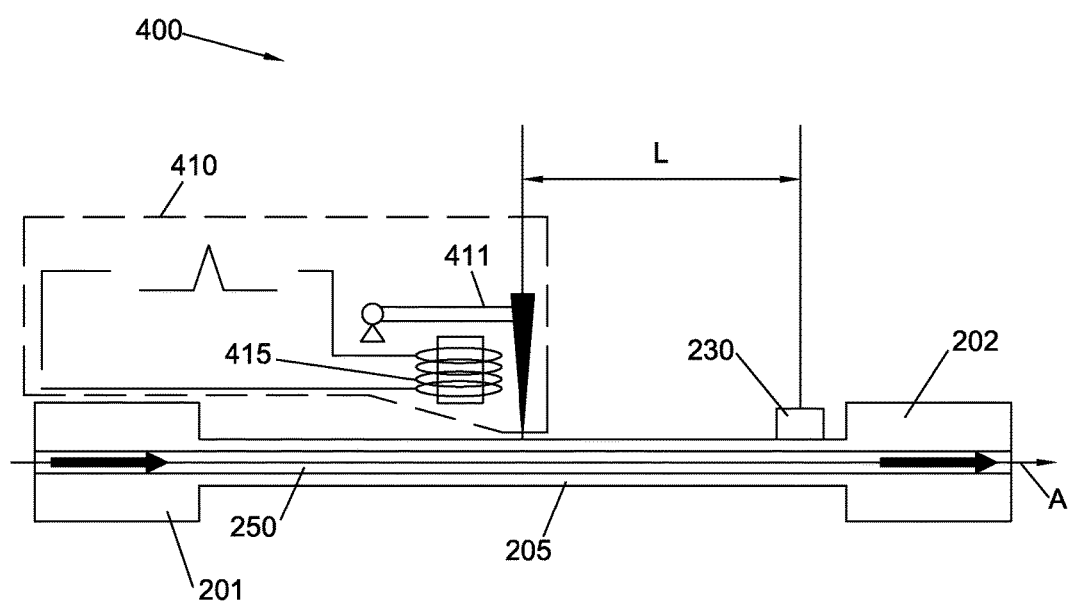
FIG. 4 shows a schematic view of a sensor for measuring the speed of sound in a fluid, according to some embodiments.

FIG. 4 shows a schematic view of a sensor 400 for measuring the speed of sound in a fluid, according to some embodiments. Sensor 400 is similar to sensors 100 and 300, except that an electromagnetic hammer 410 to strike the frame 205 is used to generate the acoustic impulse signal. Sensor 400 includes frame 205, frame endings 201 and 202, and fluid 250 having a flow rate as described in detail above in relation to sensor 100 (cf. FIG. 2). Accelerometer 230 may be placed at a distance L from electromagnetic hammer 410, as in sensor 100. Electromagnetic hammer 410 includes a coil circuit 415 having a coil and a magnet, and a hammer 411 driven by circuit 415 to strike frame 205 and generate acoustic impulses to be detected by accelerometer 230.

Figure 5:
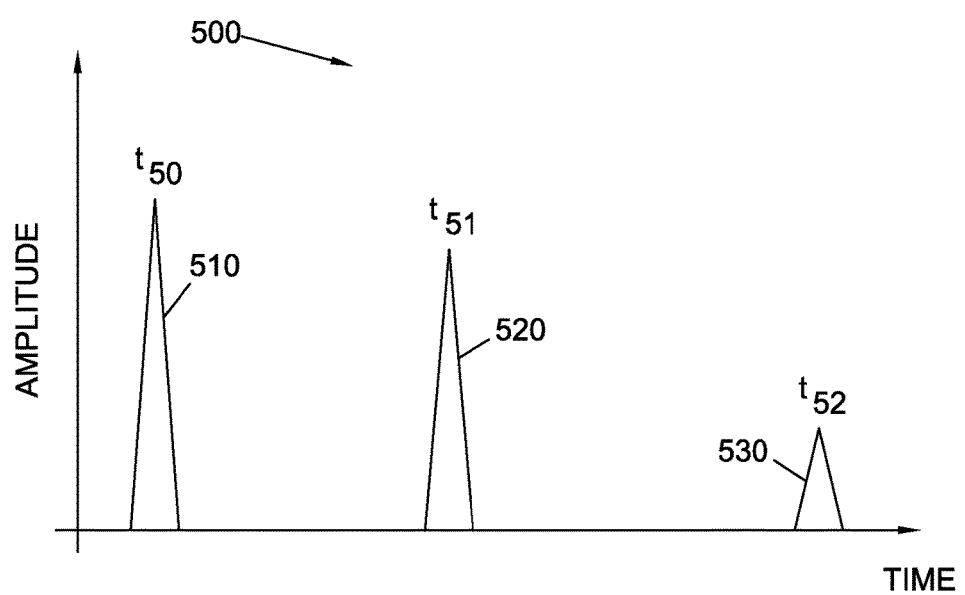
FIG. 5 shows an acoustic signal as a function of time in a detector, according to some embodiments.

FIG. 5 shows an acoustic signal 500 as a function of time in a sensor, according to some embodiments. A portion of signal 500 may be detected by accelerometer 230 in any one of sensors 100, 300, and 400 described in detail above. FIG. 5 depicts an initial impulse 510 produced by an acoustic source such as source 210, 310, or 410, described in detail above. Impulse 510 may be generated at an initial time $t_{50}$. Signal 500 may also include an impulse 520 detected by accelerometer 230 at a first detection time $t_{51}$, and an impulse 530 detected by accelerometer 230 at a second detection time $t_{52}$.

Accelerometer 230 is located at a distance L away from the acoustic source 210 and is used to detect the signal 500. Acoustic impulse 510 produced by the acoustic source 210 travels along at least two channels in sensors 100, 300, and 400. One channel is the shell of frame 205, producing impulse 520 at time $t_{51}$ in accelerometer 230. A second channel is the fluid 250, producing impulse 530 at time $t_{53}$ in accelerometer 230. Accordingly, accelerometer 230 may detect at least two distinct signals such as impulse 520 and impulse 530. At first detection time $t_{51}$, impulse 520 traveling through the shell is the first to arrive at accelerometer 230. At second detection time $t_{52}$, impulse 530 traveling through fluid 250 arrives at accelerometer 230. Generally, $t_{51}$ is less than, or equal to $t_{52}$ due to the higher speed of sound in the metallic shell of frame 205 (such as platinum or titanium) than in fluid 250.

A fluid speed of sound $v_5$ may be determined by the time lapse for pulse 530 travelling between the acoustic source and the detection in the accelerometer 230, namely $$v_5 = \frac{L}{t_{52} - t_{50}} \quad (1)$$

In some embodiments, sensor 100 is configured such that an acoustic detector including accelerometer 230 is synchronized with acoustic source 210. Thus, a synchronization mechanism ensures that a signal detected at the second detection time $t_{52}$ is originated by acoustic source 210 at initial time $t_{50}$. For example, a synchronization configuration may include an electronic trigger generated by acoustic source 210 at initial time $t_{50}$ to wake up the acoustic detector in accelerometer 230 for a time interval including first detection time $t_{51}$ and second detection time $t_{52}$.

Figure 6:
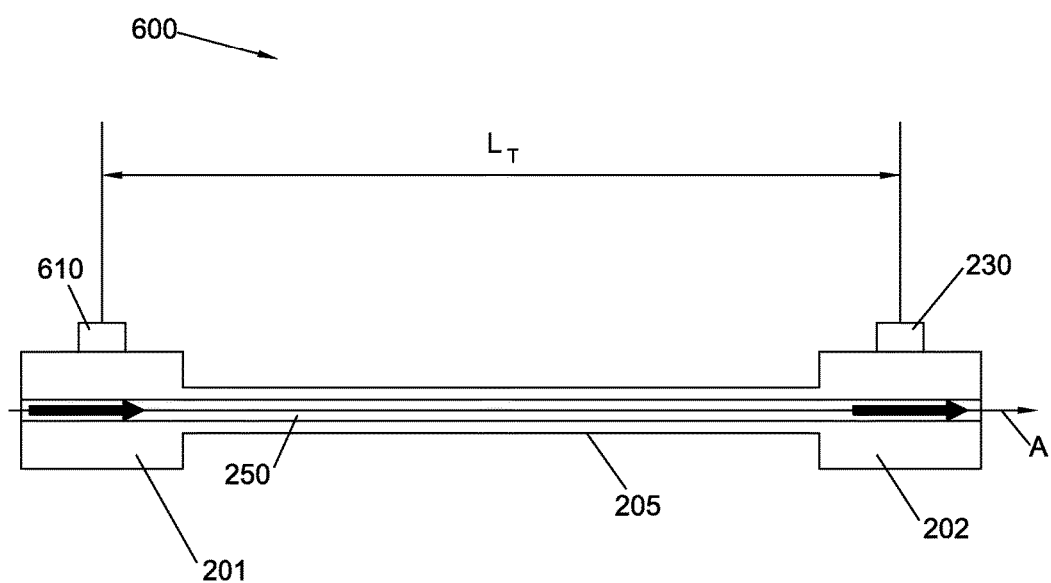
FIG. 6 shows a schematic view of a sensor for measuring the speed of sound in a fluid, according to some embodiments.

FIG. 6 shows a schematic view of a sensor 600 for measuring the speed of sound in a fluid, according to some embodiments. Acoustic source 610 is mounted to end portion 201 of frame 205. Accelerometer 230 is mounted to end portion 202 of frame 205. The distance $L_T$ between acoustic source 610 and accelerometer 230 may be similar to the total length of frame 205. In some embodiments, acoustic source 610 may be a piezoelectric material or other electro-mechanic transducer driven by an electrical circuit. Thus, in some embodiments, in addition to generating an acoustic impulse, source 610 may act as an acoustic detector by measuring a current or a voltage generated in the electrical circuit by motion transmitted by an acoustic impulse.

An impulse generated by source 610 forms at least two impulses, a first impulse travelling along frame 205 and a second impulse travelling along fluid 250. The travelling impulses are reflected back at end portions 201 and 202 of frame 205, thus creating echo impulses travelling in the opposite direction. The reflection of acoustic impulses upon reaching frame end portion 201 or frame end portion 202 is due to the impedance mismatch for acoustic propagation created by the different mass and geometry of frame end portions 201 and 202, relative to the middle portion of frame 205. Echo impulses are reflected upon reaching frame end portion 201, generating new echo impulses travelling in the direction of frame end portion 202. Each reflection reduces the energy in the impulse, so that the echo process winds down until the reflected impulses are below the measurement sensitivity of accelerometer 230. By measuring the time delay of the echo signal travelling through fluid 250, the fluid speed of sound can be measured. In some embodiments data from multiple echoes may be combined to obtain a statistically accurate result.

FIG. 7A shows a first acoustic signal 700A as a function of time in a detector, according to some embodiments. Signal 700A may be measured in transducer 610 according to embodiments of a sensor such as sensor 600 (cf. FIG. 6). Impulse 710 is generated at initial time $t_{70}$ in source 610. A first echo impulse 720 is received back at a first detection time $t_{71}$ in source 610. Echo impulse 720 may be travelling along the metallic shell of frame 205. Echo impulse 730 is received at a second detection time $t_{72}$ in source 610. Echo impulse 730 may be travelling through fluid 250. A second echo impulse 740 travelling through the metallic shell of frame 205 may be received at a third detection time $t_{73}$ in source 610. Echo impulse 750 is received at a fourth detection time $t_{74}$ in source 610 and may be the second reflection of impulse 730. A fluid speed of sound $v_7$ according to some embodiments may thus be found as $$v_7 = \frac{2L_T}{t_{74} - t_{72}} \quad (2)$$

In Eq. 2, a factor of 2 accounts for the back-and-forth travel of echo impulse 750 along frame 205, during time interval $t_{74} - t_{72}$.

FIG. 7B shows a second acoustic signal 700B as a function of time in a detector, according to some embodiments. Signal 700B may be measured in accelerometer 230 according to embodiments of a sensor such as sensor 600 (cf. FIG. 6). Impulse 710 is generated at initial time $t_{70}$ in source 610. A first impulse 760 is received at a first detection time $t_{17}$ in accelerometer 230. Impulse 760 may be travelling along frame 205. Impulse 770 is received at a second detection time $t_{27}$ in accelerometer 230. Impulse 770 may be travelling through fluid 250. A second echo impulse 780 travelling through the metallic shell of frame 205 may be received at a third detection time $t_{37}$ in accelerometer 230. Echo impulse 790 is received at a fourth detection time $t_{47}$ in accelerometer 230 and may be the second reflection of impulse 770, travelling through fluid 250.

Using at least two acoustic signals such as signals 700A and 700B the travel time of sound in opposite directions along sensor 600 may be determined. When there is a fluid flowing in a given direction inside sensor 600, one of the pulses may travel in the fluid flow direction and the travel time may be shorter compared to the travel time of a corresponding echo pulse traveling against the fluid flow direction. By measuring the difference in speed of the pulse relative to that of its echo the fluid flow speed may be determined. Knowledge of the fluid flow speed and the cross section of sensor 600 allow the determination of the fluid flow rate $F_r$ through sensor 600 (e.g. in cubic feet per minute ft³/min).

$$F_r = L \cdot A \cdot \left| \frac{1}{|t_{72} - t_{27}|} - \frac{1}{|t_{27} - t_{70}|} \right| \qquad (3)$$

where A is the flow cross sectional area, approximately equal to the cross section of sensor 600. In some embodiments, other combination of signal timings may be used and averaged, in order to obtain a more accurate value of the flow rate. For example, time difference $|t_{74} - t_{47}|$ may be averaged with time difference $|t_{72} - t_{27}|$, in Eq. 3.

Figure 8:
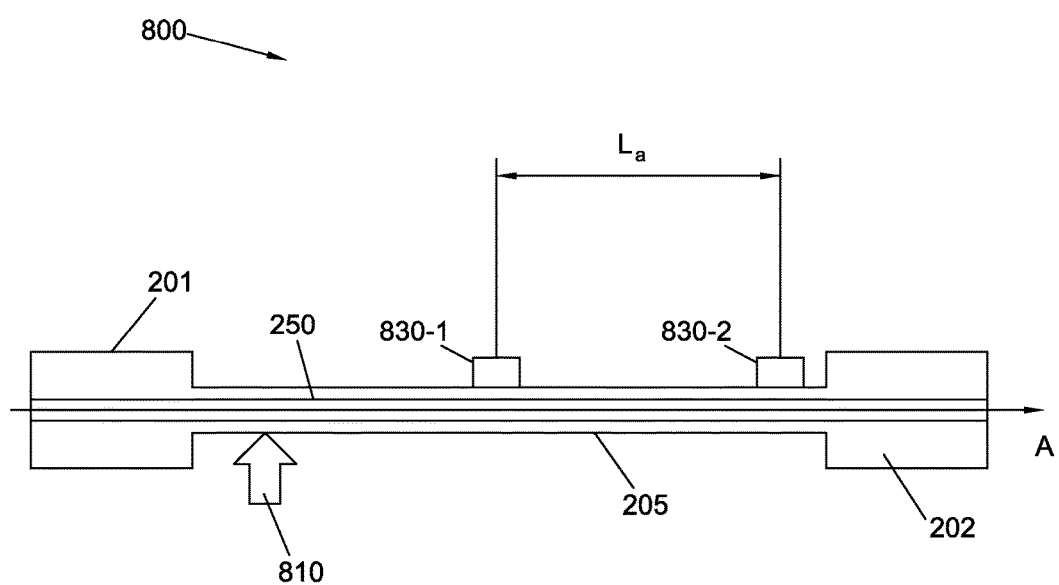
FIG. 8 shows a schematic view of a sensor for measuring the speed of sound in a fluid, according to some embodiments.

FIG. 8 shows a schematic view of a sensor 800 for measuring the speed of sound in a fluid, according to some embodiments. Sensor 800 uses two (2) accelerometers 830-1 and 830-2 to measure the speed of sound in a fluid. Use of two accelerometers provides a speed of sound measurement that is independent of the mechanism used for the acoustic source 810. Furthermore, in some embodiments acoustic source 810 may be external to sensor 800. For example, a tap produced during operation of a tool in well bore 111, or any other perturbation to drill string 112 may produce a sufficiently strong impulse signal detected by accelerometers 830-1 and 830-2, so that the two signals may be compared in order to extract the fluid speed of sound.

Sensor 800 includes a first accelerometer 830-1 and a second accelerometer 830-2 mounted in the middle portion of frame 205. The first accelerometer 830-1 and the second accelerometer 830-2 may be separated by a distance, $L_a$. While FIG. 8 illustrates two accelerometers, additional accelerometers may be used according to embodiments consistent with the present disclosure. For example, additional accelerometers may be spaced a known distance apart from each other. An acoustic signal is created by acoustic source 810 placed at any point along frame 205. In some embodiments, acoustic source 810 may be as source 210, as electromagnetic hammer 410, as an accelerometer 230, or as any other electro-mechanic transducer in source 610.

Acoustic signals obtained in embodiments including at least two (2) accelerometers independent from an acoustic source (cf. FIG. 8) may be as described in detail below in reference to FIG. 9.

Figure 9:
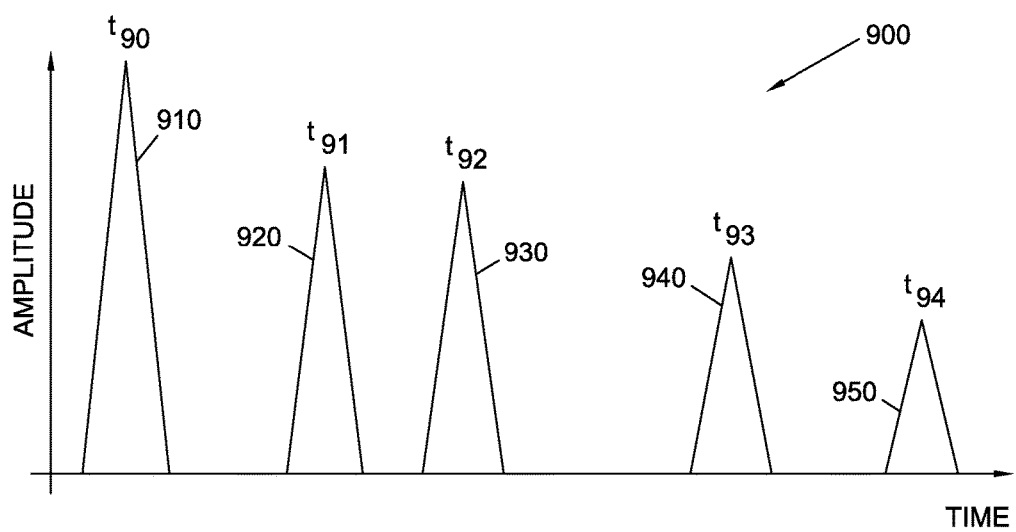
FIG. 9 shows an acoustic signal as a function of time in a detector, according to some embodiments.

FIG. 9 shows an acoustic signal 900 as a function of time in a detector, according to some embodiments. An impulse 910 is generated at time $t_{90}$, producing a frame impulse and a fluid impulse. The frame impulse generates impulse signal 920 at time $t_{91}$ in accelerometer 830-1 and impulse signal 930 in accelerometer 830-2. The fluid impulse generates impulse signal 940 at time $t_{93}$ and impulse signal 950 at time $t_{94}$ in accelerometer 830-2. Thus, a fluid speed of sound $v_9$ may be obtained as $$v_9 = \frac{L_a}{t_{94} - t_{93}} \qquad (4)$$

Embodiments as disclosed herein measure a fluid speed of sound regardless of the time or position of the excitation. Eq. 4 uses knowledge of the positions of the two accelerometers and the time of arrival of a signal to each of them, $t_{94}$ and $t_{93}$, to determine fluid speed of sound. Some embodiments may include more accelerometers to improve the accuracy of the measurement. For example, by using more accelerometers a statistical analysis may be performed with a distribution of fluid speed of sound measurements.

Some embodiments may use alternatives to accelerometer 230 or accelerometer 830-1 and 830-2 to detect an acoustic impulse. For example, some embodiments may include piezoelectric detectors or strain gauges to detect hoop stress as the pressure front passes the detector. Embodiments of a sensor such as sensors 100, 300, 400, 600, and 800 may be implemented anywhere along the drill string 112 that is accessible to a section of a flow line in a downhole tool.

Accordingly, embodiments of a sensor such as sensor 100, 300, 400, 600, and 800 provide a direct measurement of fluid speed of sound under downhole conditions. A sensor consistent with the present disclosure may be applicable to existing vibrating density sensors, such as sensor 100 (cf. FIG. 2). Sensors consistent with the present disclosure may be implemented anywhere along a flow line in a WFT or a LWDFT. Some embodiments provide a measurement of a drilling fluid speed of sound by sampling the borehole fluid in acoustic logging tools.

Figure 10:
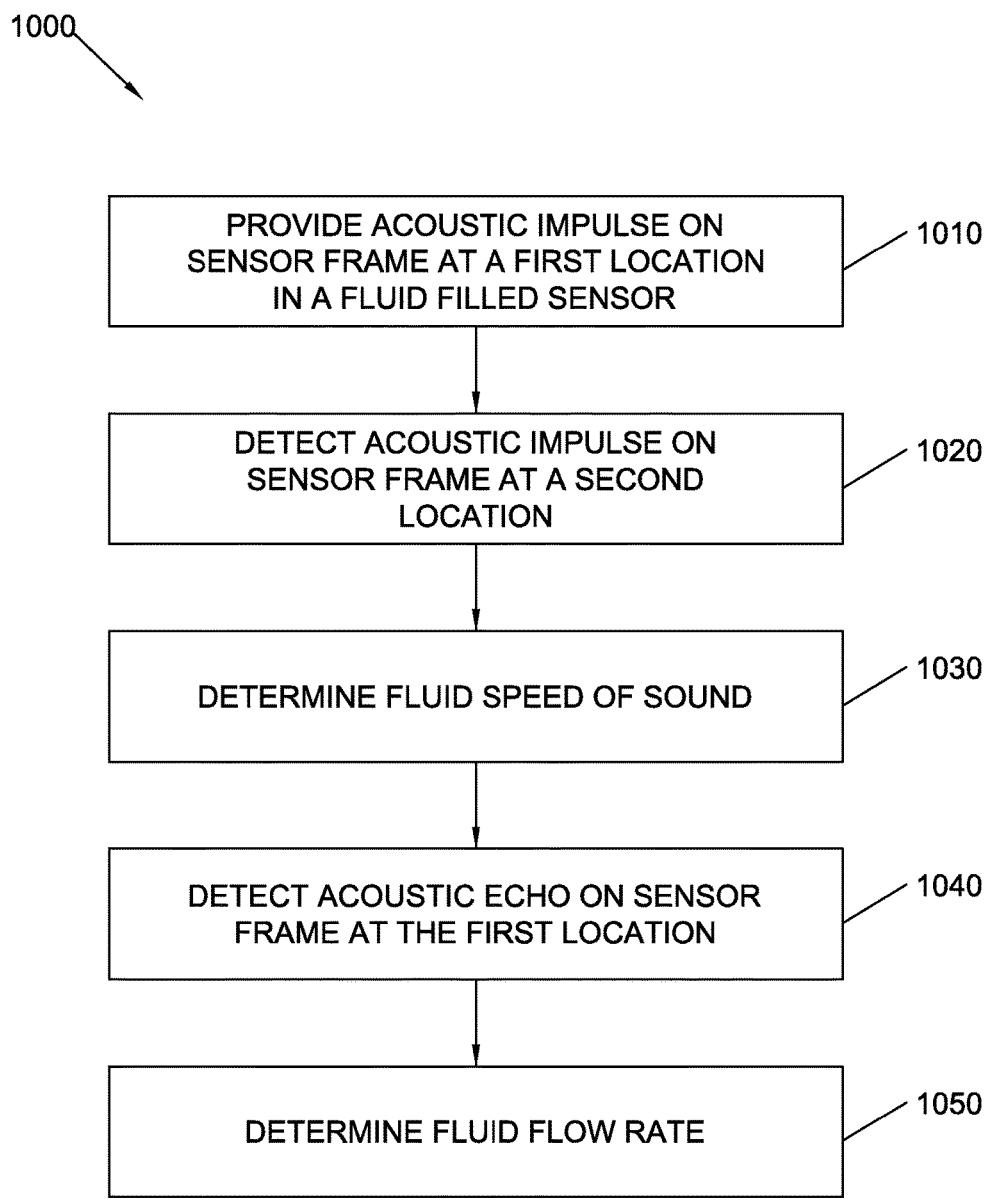
FIG. 10 shows a flow chart for a method to determine the speed of sound in a fluid, according to some embodiments.

FIG. 10 shows a flow chart for a method 1000 to determine the speed of sound in a fluid, according to some embodiments. Steps in method 1000 may be performed in part or in full by controller 105 using processor circuit 106 and memory circuit 107 to control sensor 100 (cf. FIGS. 1A and 1B). Thus, controller 105 may send commands stored in memory circuit 107 to be executed by sensor 100. As a result of method 1000, sensor 100 may provide signals and data to processor circuit 106 in controller 105. Processor circuit 106 may perform algorithms and operations on the data and store the results in memory circuit 107, according to some embodiments.

In step 1010 an acoustic impulse is provided on sensor frame 205 at a first location. The acoustic impulse may be provided by an acoustic source as source 210, 310, 410, 610, and 810 described in detail above (cf. FIGS. 2-8). The sensor in step 1010 is filled with fluid that may be a formation fluid from a borehole in a WFT or an LWDFT application. In step 1020 an acoustic impulse is detected on the sensor frame at a second location. In some embodiments, step 1020 may be performed by a detector such as accelerometer 230 (cf. FIG.

2), or another electromechanical transducer. The acoustic impulse in step 1020 may be as impulse 770 detected at time $t_{72}$ (cf. FIG. 7A). In step 1030 a fluid speed of sound is determined. For example, step 1030 may include using any one of Eqs. 1-4 and the signal detected in step 1020. In some embodiments, method 1000 may include step 1040 to detect an acoustic echo on the sensor frame at the first location. The acoustic echo may be as echo signal 730 at an echo time $t_{72}$ (cf. FIG. 7A), detected in source 610. In step 1050 a fluid flow rate is determined using the impulse time (e.g., $t_{72}$) and an echo time (e.g., $t_{27}$) (cf. Eq. 3).

In some embodiments, the fluid flow rate in step 1050 may be performed prior to determining the fluid speed of sound in step 1030. Thus, when the flow rate measured (e.g. by using Eq. 3) in step 1050 is measurable above an error tolerance of the sensor, then step 1030 includes subtracting the speed of fluid flow from the speed of the acoustic impulse, to obtain the fluid speed of sound.

FIG. 11 shows a flow chart for a method 1100 to determine physical properties of a fluid and of a downhole formation, according to some embodiments. Steps in method 1100 may be performed in part or in full by a controller (e.g., controller 105 in FIG. 1) using a processor circuit (e.g., processor circuit 106 in FIG. 1) and a memory circuit (e.g., memory circuit 107 in FIG. 1) to control a sensor (e.g., sensor 100 in FIG. 1). Thus, a controller may send commands stored in a memory circuit to be executed by a sensor, to perform the steps in method 1100. Determination of physical properties of the fluid and the down hole formation in method 1100 may be performed by algorithms stored in the memory circuit and running in the processor circuit. The processor circuit may store in the memory circuit the physical properties of the fluid and the downhole formation obtained from method 1100.

In step 1110 a speed of sound in a fluid is determined. In some embodiments, step 1110 may include performing steps 1010 through 1030 in method 1000, described in detail above (cf. FIG. 10). Furthermore, in some embodiments step 1110 may include storing the speed of sound value in the memory circuit. In step 1120 a fluid density is determined. In some embodiments, step 1120 includes generating and detecting an acoustic signal in a sensor at a frequency scanned through a certain bandwidth. Further, step 1120 may include finding a frequency that maximizes the amplitude of the detected acoustic signal, and using this frequency to determine a fluid density. In step 1130 a GOR in the fluid is determined. According to some embodiments, a GOR may be determined by looking at a previously determined linear relation between GOR values and speed of sound values. For example, the linear relation between GOR values and speed of sound values may be previously stored in the memory circuit as a lookup table. In step 1140 a dew point in the fluid is determined. For example, if the GOR found in step 1130 indicates that the fluid contains mostly a gas (50% or more, by volume), then a measurement of the speed of sound in a fluid may be used to find a dew point in the fluid in step 1130. In step 1145 a bubble point in the fluid is determined. For example, if the GOR found in step 1130 indicates that the fluid contains mostly a liquid (50% or more, by volume), then a measurement of the speed of sound in a fluid may be used to find a bubble point in the fluid in step 1145. A measurement of the speed of sound in a fluid, v, in step 1145 may be performed using a lookup table, or a formula, as expressed below:

$$v = \left[\left(\frac{c_p}{c_v}\right)\left(\frac{RT}{M_r}\right)\left(Z + \rho\left(\frac{\partial Z}{\partial \rho}\right)_T\right)\right]^{0.5} \quad (5)$$

Where $c_p$ and $c_v$ are the constant volume and constant pressure heat capacities of the gas, respectively. In Eq. 5, T is temperature, p is density, and Z is the compressibility factor. Equation 5 shows that the speed of sound depends on density, ρ. At both dew point and bubble point, the density of the fluid undergoes change. Thus associated with this change, the speed of sound will also change. Monitoring changes in density enables one to identify the dew point in gas and bubble point in liquid.

In step 1150 a shear anisotropy, γ, in a geological formation (e.g., geological formation 117 in FIG. 1) is determined. Shear wave anisotropy, γ, in step 1150 may be related to a number of important parameters in a gas shale. For example, in some embodiments the shear wave anisotropy may be used to determine a formation composition, including the depositional history and the amount and maturity of hydrocarbons in a shale. Shear anisotropy may be measured for Vertical Transverse Isotropic (VTI) formations, such as shown in FIG. 1, where the formation has a transversal symmetry across planes 150. In some embodiments, the shear anisotropy is determined by the following equation:

$$\gamma = \frac{C_{66} - C_{44}}{2 \cdot C_{44}} \quad (6)$$

Where $C_{66}$ and $C_{44}$ are components in a 6×6 shear tensor, C, relating the strain of a material to the stress inducing the strain. $C_{66}$ is the anisotropic shear modulus in a layered formation, such as in a gas shale. Dipole shear wave log techniques measure component $C_{44}$ of shear tensor, C. In some embodiments of method 1100, a Stoneley wave is used to estimate component $C_{66}$. Furthermore, Stoneley wave speed dependence on component $C_{66}$ is also determined by the mud/fluid speed of sound in the borehole. Thus, step 1150 includes using the speed of sound in the mud/fluid to determine $C_{66}$ using the measured Stoneley wave speed from acoustic logs. $C_{66}$ is also the appropriate shear modulus component for the calculation of various fracture parameters, such as maximum and minimum horizontal stresses, rather than $C_{44}$.

Embodiments described herein are exemplary only. One skilled in the art may recognize various alternative embodiments from those specifically disclosed. Those alternative embodiments are also intended to be within the scope of this disclosure. As such, the embodiments are limited only by the following claims.

What is claimed is:

1. An apparatus for measuring a speed of sound in a fluid in a well bore, the apparatus comprising:
    a frame adapted to receive the fluid therethrough;
    an acoustic source mounted on the frame and configured to generate one or more acoustic impulses;
    an accelerometer configured to detect movement of the frame caused by the generated one or more acoustic impulses and determine a time at which the impulses arrive at the accelerometer, the accelerometer disposed proximate the frame at a known distance from the acoustic source; and
    processing circuitry coupled to the acoustic source and accelerometer to perform operations comprising:

providing, at a first time, an acoustic impulse to a first predetermined location of the frame having a hollow core at least partially filled with a fluid;

detecting, at a second predetermined location, a first arrival time of the acoustic impulse propagated along the frame;

detecting, at the second predetermined location, a second arrival time of the acoustic impulse propagated along the fluid; and determining a speed of sound in the fluid using a time interval between the first and second arrival times.

2. The apparatus of claim 1 wherein the accelerometer comprises an optical mechanism.

3. The apparatus of claim 1 wherein the accelerometer comprises an electro-mechanical transducer.

4. The apparatus of any one of claims 1 through 3 wherein the acoustic source comprises a coil circuit and a magnet.

5. The apparatus of any one of claims 1 through 3 wherein the accelerometer is synchronized with the acoustic source so that the accelerometer detects the time at which the signal arrives, at a detection time, the one or more signals produced at an initial time by the acoustic source.

6. The apparatus of any one of claims 1 through 3 wherein the frame includes a first end portion and a second end portion each having more mass and a different geometry than a middle portion of the frame.

7. The apparatus of any one of claims 1 through 3 wherein the accelerometer comprises two accelerometers placed at a known distance from one another.

8. The apparatus of any one of claims 1 through 3 wherein the acoustic source comprises an electromagnetic hammer.

9. The apparatus of claim 1 wherein the acoustic source comprises an electro-mechanic transducer.

10. The apparatus of claim 9 wherein the electro-mechanic transducer comprises a piezoelectric material.

11. The apparatus of any one of claims 1 through 3 wherein the frame is made of a material selected from the group consisting of a metal, a glass, and a ceramic material.

12. A method to determine fluid speed of sound comprising:

providing an acoustic impulse to a first location of a sensor frame having a hollow core at least partially filled with a fluid;

detecting, at a second location, a first arrival time of the acoustic impulse propagated along the sensor frame;

detecting, at the second location, a second arrival time of the acoustic impulse propagated along the fluid; and determining a fluid speed of sound using the first arrival time and the second arrival time.

13. The method of claim 12 wherein determining a fluid speed of sound comprises determining a distance between the first location and the second location.

14. The method of claim 12 or 13 further comprising:

detecting, at an echo time, an acoustic echo from the acoustic impulse at the first location;

determining the speed of the acoustic impulse using the second time and the echo time;

determining a speed of the acoustic echo; and comparing the speed of the acoustic impulse to the speed of the acoustic echo to determine a fluid flow rate.

15. The method of claim 12, wherein determining the fluid speed of sound further comprises utilizing a known speed of sound of the frame.

16. The apparatus of claim 1, wherein determining the fluid speed of sound further comprises:

determining a distance between the first and second predetermined location; and utilizing the determined distance and a known speed of sound of the frame to determine the fluid speed of sound.

* * * * *